(12) United States Patent
Keri et al.

(10) Patent No.: US 6,936,731 B2
(45) Date of Patent: Aug. 30, 2005

(54) PRAVASTATIN SODIUM SUBSTANTIALLY FREE OF PRAVASTATIN LACTONE AND EPI-PRAVASTATIN, AND COMPOSITIONS CONTAINING SAME

(75) Inventors: Vilmos Keri, Debrecen (HU); Lajos Deak, Debrecen (HU); Ilona Forgacs, Debrecen (HU); Csaba Szabo, Debrecen (HU); Arvai Edit Nagyne, Debrecen (HU)

(73) Assignee: TEVA Gyógyszergyár Részvénytársaság, Debrecen (HU)

( * ) Notice: Subject to any disclaimer, the term of this patent is extended or adjusted under 35 U.S.C. 154(b) by 0 days.

(21) Appl. No.: 09/971,746

(22) Filed: Oct. 5, 2001

(65) Prior Publication Data

US 2002/0082295 A1 Jun. 27, 2002

Related U.S. Application Data

(60) Provisional application No. 60/238,278, filed on Oct. 5, 2000.

(51) Int. Cl.$^7$ .......................... C07C 67/02; C12P 17/06
(52) U.S. Cl. .................... 560/256; 560/119; 560/188; 435/125; 435/169
(58) Field of Search ................. 546/119, 188, 546/256; 435/125, 169; 560/256, 119, 188

(56) References Cited

U.S. PATENT DOCUMENTS

| 4,346,227 A | * | 8/1982 | Terahara et al. ............ 560/119 |
| 5,202,029 A |   | 4/1993 | Haytko et al. |
| 5,942,423 A |   | 8/1999 | Demain et al. |
| 6,695,969 B1 | * | 2/2004 | Grahek et al. .............. 210/656 |

FOREIGN PATENT DOCUMENTS

| WO | WO 92/16276 | * | 10/1992 |
| WO | WO 99/42601 | * | 8/1999 |
| WO | WO 00/17182 |   | 3/2000 |
| WO | WO0017182   | * | 3/2000 |

OTHER PUBLICATIONS

Merck Index, 11$^{th}$ Edition, p. 1222.*

* cited by examiner

*Primary Examiner*—Cecilia J. Tsang
*Assistant Examiner*—Hector Reyes
(74) *Attorney, Agent, or Firm*—Kenyon & Kenyon

(57) ABSTRACT

The present invention provides pravastatin sodium substantially free of pravastatin lactone and epiprava, the C-6 epimer of pravastatin. The present invention further provides a novel process for recovering pravastatin sodium from a fermentation broth in such high purity. The process includes the stages of forming an solution of the compound by extraction, obtaining an ammonium salt of pravastatin from the solution, purifying the ammonium salt of the compound and transposing the salt of the compound to pravastatin sodium.

9 Claims, No Drawings

PRAVASTATIN SODIUM SUBSTANTIALLY FREE OF PRAVASTATIN LACTONE AND EPI-PRAVASTATIN, AND COMPOSITIONS CONTAINING SAME

CROSS-REFERENCE TO RELATED APPLICATION

The present application claims priority under 35 U.S.C. 119(e) to U.S. Provisional Application No. 60/238,278, filed Oct. 5, 2000, which is incorporated herein by reference.

FIELD OF THE INVENTION

The present invention relates to statins and more particularly to pravastatin sodium and processes for isolating it as a product of enzymatic hydroxylation of compactin from a fermentation broth.

BACKGROUND OF THE INVENTION

Statin drugs are currently the most therapeutically effective drugs available for reducing the level of LDL in the blood stream of a patient at risk for cardiovascular disease. This class of drugs includes pravastatin as well as compactin, lovastatin, simvastatin, fluvastatin and atorvastatin.

Pravastatin is the common medicinal name of the chemical compound [1S-[1α(β*,δ*)2α,6α,8β(R*),8aα]]-1,2,6,7,8,8a-hexahydro-β, δ, 6-trihydroxy-2-methyl-8-(2-methyl-1-oxobutoxy)-1-naphthalene-heptanoic acid. (CAS Registry No. 81093-370.) The molecular structure of pravastatin is represented by Formula (Ia) where R=OH. The lactone form is represented by Formula (Ib), with atoms labeled to indicate numbering of the atoms.

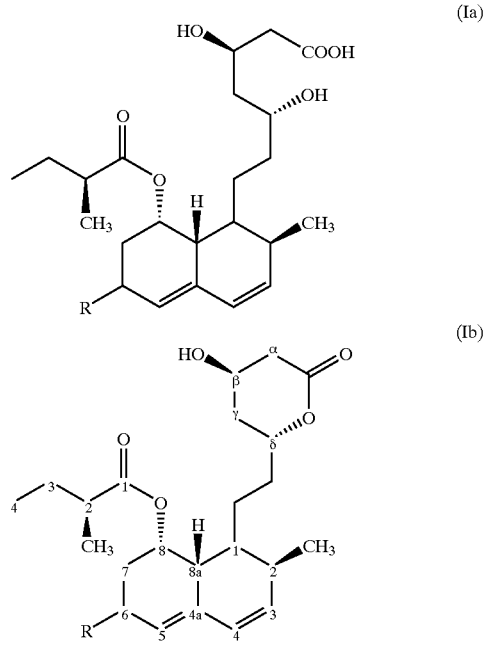

Pravastatin, compactin (Formula Ia, R=H), lovastatin (Formula Ia, R=CH$_3$), simvastatin, fluvastatin and atorvastatin each possess an alkyl chain that is terminated by a carboxylic acid group and that bears two hydroxyl groups at the β and δ positions with respect to the carboxylic acid group. The carboxylic acid group and the hydroxyl group at the δ position are prone to lactonize as shown in formula (Ib). Lactonizable compounds like the statins may exist in the free acid form or the lactone form or as an equilibrium mixture of both forms. Lactonization causes processing difficulties in the manufacture of statin drugs because the free acid and the lactone forms of the compounds have different polarities. A method of purifying one form is likely to remove the other form along with the impurities resulting in a lower yield. Consequently, great care must ordinarily be exercised when handling lactonizable compounds in order to isolate them in high yield.

Presently, the most economically feasible method of making pravastatin is by microbial hydroxylation of compactin at the C-6 position. Although enzymatic processes are highly stereoselective, it is common for pravastatin sodium obtained after isolation from a fermenation broth to be contaminated with a significant amount of the C-6 epimer of pravastatin ("epiprava"). The C-6 position is bis-allylic and, hence, the C-6 atom is prone to epimerize. Careful control of pH and other conditions during isolation of pravastatin is required in order to minimize epimerization. Known methods of isolating pravastatin from a fermentation broth either are ill-suited for isolating pravastatin as its sodium salt or produce pravastatin sodium contaminated with significant amounts of pravastatin lactone and/or epiprava. The present invention meets a need in the art for an efficient method of isolating pravastatin sodium from a fermentation broth in high purity, in high yield, on a preparative scale and without the need for chromatographic purification.

SUMMARY OF THE INVENTION

The present invention provides pravastatin sodium substantially free of pravastatin lactone and epiprava, the C-6 epimer of pravastatin. The invention further provides a process that can be practiced on an industrial scale for producing such substantially pure pravastatin sodium.

A preferred embodiment of the process involves extraction of pravastatin from an aqueous fermentation broth into an organic solvent, back-extraction of pravastatin into a basic aqueous solution and a re-extraction into an organic solvent, resulting in an organic solution containing pravastatin. The present invention provides for obtaining pravastatin from the organic solution as a salt and then purification by recrystallization of the salt. The recrystallized salt is then transposed to form pravastatin sodium salt and any excess sodium ions are scavenged with an ion exchange resin. The sodium salt of pravastatin may then be isolated in a highly pure state from solution by recrystallization, lyophilization or other means.

DETAILED DESCRIPTION OF THE INVENTION

The present invention provides pravastatin sodium substantially free of pravastatin lactone and epiprava and a downstream process for isolating pravastatin sodium from a fermentation broth in such high purity.

Enzymatic Hydroxylation of Compactin

The enzymatic hydroxylation broth from which pravastatin is isolated can be any of the aqueous broths known for industrial scale fermentation of compactin, such as the methods described in U.S. Pat. Nos. 5,942,423 and 4,346,227. Preferably, the enzymatic hydroxylation is conducted using a living culture of *Steptomyces*, with a nutrient mixture of compactin and dextrose. If the broth is neutral or basic upon completion of the fermentation, then an acid is added to it to bring the broth to a pH of between about 1 and 6, preferably between 1 and 5.5 and more preferably between 2 and 4. Acids that may be used include hydrochloric acid, sulfuric acid, trifluoroacetic acid or any other protic acid, preferably one having a pH of less than 1 as a 1M solution in water. Acidification of the fermentation broth converts any pravastatin carboxylate salts in the broth to the free acid and/or lactone.

Isolation of Substantially Pure Pravastatin Sodium

Pravastatin is preferable first obtained from an aqueous fermentation broth in a relatively highly concentrated organic solution by a sequence of extraction and back-extraction steps. Preferably, the organic solution of pravastatin is an enriched organic solution of pravaststin.

In the first step, pravastatin is preferably extracted from the fermentation broth. $C_2$–$C_4$ alkyl formates and $C_1$–$C_4$ alkyl esters of $C_2$–$C_4$ carboxylic acids are capable of efficient extraction of pravastatin from an aqueous fermentation broth. The alkyl group may be linear, branched or cyclic. Preferred esters include ethyl formate, n-propyl formate, i-propyl formate, n-butyl formate, s-butyl formate, i-butyl formate, t-butyl formate, methyl acetate, ethyl acetate, n-propyl acetate, i-propyl acetate, n-butyl acetate, s-butyl acetate, i-butyl acetate, t-butyl acetate, methyl propionate, ethyl propionate, n-propyl propionate, i-propyl propionate, butyl propionate, methyl butyrate, ethyl butyrate, n-propyl butyrate, i-propyl butyrate, butyl butyrates, methyl isobutyrate, ethyl isobutyrate, propyl isobutyrates and butyl isobutyrates. Of these preferred organic solvents we have found that ethyl acetate, i-butyl acetate, propyl acetate and ethyl formate are especially well suited. The most preferred extraction solvent is i-butyl acetate. Other organic solvents may be substituted for the esters. Halogenated halocarbons, aromatic compounds, ketones and ethers may be used, such as dichloromethane, chloroform, carbon tetrachloride, 1,2-dichloroethane, benzene, butyl methyl ketone, diethyl ether and methyl t-butyl ether.

Pravastatin is optionally back-extracted into a basic aqueous solution of pH from about 8.0 to about 9.5. The base is preferably NaOH, $NH_4OH$ or KOH, most preferably NaOH. The extraction solvent is preferably contacted with the basic aqueous solution until the amount of pravastatin in the organic phase has been substantially depleted as determined by thin layer chromatography or any other method including the subjective judgment that sufficient contacting has occurred for complete extraction. Multiple back-extractions may be performed for optimal recovery. However, a single back-extraction is highly efficient when the organic phase is i-butyl acetate. Back-extraction may be used to concentrate the pravastatin by using a volume of aqueous base that is less than the volume of the organic extract. Preferably, the back-extraction is conducted with a volume of basic aqueous solution that is less than one third of the volume of the organic extract, more preferably less than one fourth and most preferably, about one fifth the volume of the organic extract.

The aqueous solution is preferably acidified with an acid, preferably trifluoroacetic acid, hydrochloric acid, sulfuric acid, acetic acid, or phosphoric acid, more preferably sulfuric acid, to a pH of about 1.0 to about 6.5, more preferably about 2.0 to about 3.7.

Pravastatin is preferably re-extracted into one of the organic solvents previously described as suitable for extracting pravastatin from the fermentation broth. The organic solvent may be, but need not be, the same solvent used to extract pravastatin from the fermentation broth. In this re-extraction, further enrichment of pravastatin may be accomplished by re-extracting into an amount of organic solvent that is preferably less than about 50% (v/v) of the aqueous extract, more preferably from about 33% (v/v) to about 20% (v/v) and still more preferably about 25% (v/v) the volume of the aqueous extract. Pravastatin may be concentrated from 100 L of fermentation broth to 8 L of organic solution in 89% yield from the initial organic extract. It will be appreciated by those skilled in the art that a higher yield of purified pravastatin may be attained by performing multiple extractions where only a single extraction has been described in this preferred mode for practicing the invention. This preferred mode achieves a balance of solvent economy and high product yield. Deviations from this preferred mode which further enhance the yield by repeated extractions where only one has been described above do not necessarily depart from the spirit of the invention. Before proceeding to obtain pravastatin from the organic solution by "salting out," the organic solution is preferably dried, which may be done using a conventional drying agent such as $MgSO_4$, $Na_2SO_4$, $CaSO_4$, silica, perlite and the like, and optionally decolorized with activated carbon. A dried and/or decolorized organic solution is preferably then separated conventionally, as for instance by filtration or decanting.

The present invention provides obtaining solid pravastatin from the organic solution by a salting out process. As provided for herein, the salting out process preferably includes the steps obtaining solid pravastatin as a pravastatin salt. The cation of the pravastatin salt may be ammonium or an amine. Alternatively, the cation of the pravastatin salt may be an alkali metal cation. Preferred alkali metal cations include lithium, sodium and potassium.

In one embodiment of the present invention, solid pravastatin is salted out from the organic solution with ammonium or an amine. The amine may be a primary, secondary or tertiary amine. Any alkyl or aryl amine that is not so hindered as to prevent ionic interaction between the amine nitrogen and the carboxyl group of pravastatin may be used. The amines include, but are not limited to, methyl, dimethyl, trimethyl, ethyl, diethyl, triethyl and other $C_1$–$C_6$ primary, secondary and tertiary amines; and further include morpholine, N-methylmorpholine, isopropyl cyclohexyl amine, piperidine and the like. Regardless of the absence, presence or multiplicity of substitution on nitrogen, a salt formed by reaction of ammonia or an amine is hereafter referred to as an ammonium salt. Its meaning is intended to encompass salts of amines as well as a salt of ammonia.

Precipitation of the ammonium salt of pravastatin also may be induced by addition of an ammonium salt either alone or in combination with the ammonia or amine. The preferred ammonium salts are the following salts of ammonia: $NH_4Cl$, $NH_4Br$, $NH_4I$, $(NH_4)_2SO_4$, $NH_4NO_3$, $(NH_4)_3PO_4$, $(NH_4)_2S_2O_4$ and $NH_4OAc$, the most $NH_4Cl$. Ammonium salts and high boiling liquid and solid amines may be added by conventional means, preferably in an area with good ventilation, either as solids, neat liquids or solutions in aqueous or organic solvent. Addition of gaseous ammonia requires special equipment for handling caustic gases. Such equipment, including pressure vessels, regulators, valves and lines are widely available. In an especially preferred embodiment, pravastatin is obtained from the organic solution as the pravastatin salt of ammonia by addition of gaseous ammonia and $NH_4Cl$ to the organic solution.

The temperature at which the ammonia, amine and/or ammonium salt should be added can be determined by routine experimentation by conducting the reaction on a small scale and monitoring the exothermicity of the reaction. Preferably, the solution temperature is not allowed to exceed 40° C. Although temperatures as high as 80° C. may be experienced without significant decomposition of pravastatin, many organic solvents of this invention will boil at a lower temperature. When ammonia is used, the preferred temperature range is from about −10° C. to about 40° C.

In an alternative embodiment, solid pravastatin may be salted out from the organic solution as a salt of alkali metal by adding an alkali metal cation in the form of an alkali metal salt to the organic solution. Preferred alkali metal cations include lithium, sodium and potassium.

The obtained solid pravastatin may be in the form of a crystal or an amorphous precipitate.

Preferably, once formation of solid pravastatin ceases, or consumption of pravastatin is determined to be substantially complete by other means, the addition of amine or alkali metal salt should be ceased.

The present invention provides that the solid pravastatin may be in the form of a crystal. Alternatively, the solid pravastatin may be in the form of an amorphous solid.

When ammonia or a volatile amine is used, the vessel is preferably vented to disperse excess fumes. The solid pravastatin may then be isolated by filtration, decantation of the solvent, evaporation of the solvent or other such method, preferably filtration. The solid pravastatin may then be washed, preferably with i-butyl acetate and acetone.

After optionally washing the solid pravastatin, the pravastatin salt is preferably purified by one or more, or most preferably three, recrystallizations. To purify the pravastatin salt, the salt is preferably dissolved in water. The polarity of the solution is preferably decreased by addition of an anti-solvent. The anti-solvent is preferably a water-soluble organic solvent or solvent mixture in which the pravastatin salt is poorly soluble. The anti-solvent is most preferably i-butyl acetate and acetone.

The pravastatin salt may be allowed to recrystallize spontaneously, or may be induced to recrystallize by taking the further step of adding a common ion. According to the preferred process wherein pravastatin is purified as its ammonia salt, $NH_4Cl$ is added to induce recrystallization of the ammonium salt.

The recrystallization maybe performed at between about −10° C. and about 40° C., preferably between about 0° C. and about 40° C. After the pravastatin salt has been substantially recrystallized from the solution, the crystals are isolated and may be washed, for example with a 1:1 mixture of i-butyl acetate and acetone and then dried. Drying may be conducted at ambient temperature but is preferably conducted at mildly elevated temperature of less than 45° C. and preferably about 40° C. The recrystallization may optionally be repeated to good effect as shown in Examples 3 and 4. Each repetition occurs in about 92% yield.

After purification of the pravastatin salt, the cation of the pravastatin salt is preferably transposed to pravastatin sodium. While not being bound by theory, it is believed that it is advantages to transpose the cation of the pravastatin salt to pravastatin sodium because the step of transposing the counterion removes inorganic impurities.

Pravastatin is preferably liberated from the amine or alkali metal by dissolving in an aqueous solvent, acidifying with any protic acid, but preferably sulfuric acid, to a pH of about 2 to about 4, more preferably about 3.1, and extracting pravastatin with an organic solvent. The organic solvent, which may be any of the organic solvents listed above but preferably is i-butyl acetate, is optionally contacted with the acidified solution until pravastatin is substantially completely transferred to the organic phase. The organic phase is preferably separated from the aqueous phase and, after optionally washing with water to remove residues, the pravastatin is preferably back-extracted with aqueous sodium hydroxide solution at a pH of from about 7.4 to about 13.0. The back-extraction is preferably conducted at a reduced temperature of about 8 to about 10° C.

After extraction into aqueous sodium hydroxide, excess sodium cations are scavenged to attain a near 1:1 equivalence of sodium cation and pravastatin using a water insoluble ionic exchange resin. Suitable ion exchange resins are the cationic and chelate type resins, the preferred being strong and weak acid exchange resins.

Among the strong acid cationic exchange resins which may be used are those having sulfonic acid ($SO_3^-H^+$) groups. These include the commercial products Amberlite® IR-118, IR-120 252H; Amberlyst® 15, 36; Amberjet 1200 (H) (Rohm and Haas); Dowex® 50WX series, Dowex HCR-W2, Dowex 650C, Dowex Marathon C, Dowex DR-2030, and Dowex HCR-S, ion exchange resins (Dow Chemical Co.); DLAION SK 102 to DIAION SK 116 resin series and Lewatit SP 120 (Bayer). The preferred strong acid cationic exchange resins are Amberlite® 120, Dowex 50WX and DIAION SK series.

Weak acid cationic exchange resins include those which have pendant carboxylic acid groups. Weak acid cationic exchange resins include the commercial products Amberlite CG-50, IRP-64, IRC 50 and C67, Dowex CCR series, Lewatit CNP series (Bayer) and DIAION WK series (Mitsubishi), of these, the most preferred are Amberlite® IRC50, Lewatit CNP 80 and DIAION WK 10. Less preferred are the chelate type exchange resins. Some of the commercial varieties that are available include Amberlite® IRC-718, and IRC-467.

The solution containing pravastatin sodium salt and excess sodium cations may be contacted with the ion exchange resin by any method known to the art, including passage of the solution through a column or bed of the resin or by stirring a sufficient quantity of the resin in a flask with the solution. The mode of contact is not critical. After scavenging of the excess sodium ion, the pH of a pravastatin sodium solution should be in the range of about of 7 to about 10, preferably about 7.4 to about 7.8, although the pH will vary with dilution. Reduction in the pH of the pravastatin sodium solution from a higher pH to a lower pH and then leveling off of the pH at the lower level is an indication of substantial completion of scavenging excess $Na^+$ ions. After scavenging is substantially complete, the pravastatin sodium solution is preferably separated from the resin in a conventional manner. It may either be collected as the eluent from a column or bed or may be separated by filtration, decantation and the like.

Pravastatin sodium may be isolated from the pravastatin sodium solution by crystallization. Efficient crystallization may first require partial removal of the water, which can be conducted by vacuum distillation or nano-filtration. Preferably, the aqueous pravastatin sodium salt solution is concentrated from about 20 to about 50 w/v % before crystallizing. If necessary, after concentration the aqueous pravastatin sodium solution can be adjusted to a pH of between about 7 and about 10 with an ion exchange resin in $H^+$ form.

Addition of a water-soluble organic solvent or organic solvent mixture to the pravastatin sodium solution will assist the crystallization. In particular, there may be mentioned acetone and acetone/acetonitrile, ethanol/acetonitrile and ethanol/ethyl acetate mixtures. One of the most preferred solvent system for crystallizing pravastatin sodium is a 1/3/12 water/acetone/acetonitrile mixture formed by concentrating the pravastatin sodium solution to about 30 w/v % and then adding an appropriate volume of 1/4 acetone/acetonitrile mixture. The most preferred crystallization solvent mixture is water-acetone (1:15).

Pravastatin sodium also may be isolated by lyophilization of the aqueous pravastatin sodium solution.

Whether isolated by lyophilization or crystallization or other means that does not diminish the purity of the product, the pravastatin sodium that is isolated in the practice of the present inventive process is substantially free of pravastatin lactone and epiprava. As demonstrated in the examples that follow, pravastatin sodium may be isolated with less than 0.5% (w/w) contamination by pravastatin lactone and less than 0.2% (w/w) contamination by epiprava. Pravastatin sodium further may be isolated with less than 0.2% (w/w) pravastatin lactone and 0.1% epiprava by adhering to the preferred embodiments of the invention, two of which are exemplified in Examples 1 and 3

The highly pure pravastatin sodium produced by the present inventive method is preferably useful for hypercholesteremia therapy and for this purpose it can administered to a mammalian patient by any route of administration. A daily oral regimen is the most preferred prescribed method of administration. In human subjects with normal hepatic function and moderate body weight, a reduction in serum cholesterol levels is typically observed with daily oral dosages of 10 mg or more pravastatin sodium. The quantity of the highly pure pravastatin sodium administered may be any effective amount. Preferred oral dosages of the present invention contain from about 10 mg to about 40 mg of pravastatin sodium. Oral dosages include tablets, pills, capsules, troches, sachets, suspensions, powders, lozenges, elixirs and the like. The substantially pure pravastatin sodium may be administered by any route but the most preferred route of administration is oral.

The highly pure pravastatin may be administered either alone or in a composition with pharmaceutical excipients. Whether administered alone or in a composition, the highly pure pravastatin sodium of the invention may be in the form of a solution or a solid such as a powder, granules, aggregates or any other solid form.

The compositions of the present invention include compositions for tableting. Tableting compositions may have few or many excipients depending upon the tableting method used, the release rate desired and other factors. For example, compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and calcium diphosphate and other diluents known to the pharmaceutical industry. Yet other suitable diluents include waxes, sugars and sugar alcohols like mannitol and sorbitol, acrylate polymers and copolymers, as well as pectin, dextrin and gelatin.

Further tableting excipients include binders, such as acacia gum, pregelatinized starch, sodium alginate, glucose and other binders used in wet and dry granulation and direct compression tableting processes. Excipients that may also be present in a solid composition of the novel forms of pravastatin sodium further include disintegrants like sodium starch glycolate, crospovidone, low-substituted hydroxypropyl cellulose and others. Additional excipients include tableting lubricants like magnesium and calcium stearate and sodium stearyl fumarate; flavorings; sweeteners; preservatives; pharmaceutically acceptable dyes and glidants such as silicon dioxide.

Capsule dosages will contain the solid composition within a capsule which may be made of gelatin or other encapsulating material. Tablets and powders may be coated. Tablets and powders may be coated with an enteric coating. The enteric-coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The highly pure pravastatin sodium may also be administered in injectable dosages as a solute or suspended solid in a sterile solution or suspension. Suitable carriers for sterile injectable dosages include water and oils.

Although the following examples illustrate the practice of the present invention in some of its embodiments, the examples should not be construed as limiting the scope of the invention. Other embodiments will be apparent to one skilled in the art from consideration of the specification and examples. It is intended that the specification, including the examples, is considered exemplary only, with the scope and spirit of the invention being indicated by the claims which follow.

EXAMPLES

Example 1

Purification of Pravastatin

The fermentation broth (100 L) was acidified to from about 2.5 to about 5.0 by addition of sulfuric acid. The acidified fermentation broth was extracted with i-butyl acetate (3×50 L). The yield of i-butyl acetate extraction was found to be 95% by HPLC analysis calibrated to the internal standard in the broth. The combined i-butyl acetate phases were then extracted with water (35 L) at about pH 7.5 to about pH 11.0 by addition of concentrated ammonium hydroxide. The resulting aqueous pravastatin solution was then reacidified to a pH of about 2.0 to about 4.0 by addition of 5M sulfuric acid and back-extracted with i-butyl acetate (8 L). The resulting solution of pravastatin in i-butyl acetate was partially dried over Perlite and $Na_2SO_4$. The pravastatin solution was decanted and then filtered from the drying agents and decolorized over activated charcoal (1.7 g). The solution was then filtered to remove the charcoal and transferred to a flask equipped with a gas inlet.

Ammonia gas was then introduced into the headspace above the solution with rapid stirring. The precipitated crystals of ammonium pravastatin carboxylate salt were collected by filtration and washed with i-butyl acetate and then acetone which yielded pravastatin ammonium salt in about 94% purity as determined by HPLC coupled with UV absorbance measured at $\lambda=238$ nm.

The pravastatin ammonium salt was further purified by crystallization from a saturated ammonium chloride solution as follows. The pravastatin salt containing 162 g of active substance was dissolved in water (960 ml) and diluted with acetone (96 ml) and i-butyl acetate (96 ml) at about 35–40° C. The solution was cooled to about 30–32° C. and pravastatin ammonium was induced to crystallize by addition of solid $NH_4Cl$ until further addition resulted in no apparent increase in crystal formation. After adding ammonium chloride, the solution is cooled to about 0–26° C. The pravastatin ammonium crystals were collected by filtration and washed with i-butyl acetate and acetone, as before, and then dried at about 40° C. The resulting pravastatin ammonium salt crystals (155.5 g) were obtained in about 98% purity as determined by HPLC employing the aforementioned conditions.

The pravastatin ammonium salt was further purified by another crystallization as follows. The pravastatin ammonium salt (155.5 g of active substance) was dissolved in water (900 ml). Isobutanol (2 ml) was added and then the pH was raised to about pH 10 to about pH 13.7 by addition of a concentrated solution of sodium hydroxide and the solution was stirred for 30 min. at ambient temperature. The solution was neutralized to a pH of about 7 by addition of sulfuric acid and crystallization of pravastatin ammonium was induced by addition of solid $NH_4Cl$. The crystals (150 g) were collected by filtration and washed with acetone. Pravastatin ammonium was found to be about 99.3% pure by HPLC detection using the above-described conditions.

The pravastatin ammonium was then transposed to the sodium salt as follows. The pravastatin ammonium salt crystals were dissolved in water (1800 ml). i-butyl acetate (10.5 L) was added. The solution was then acidified to a pH of between from about pH 2 to about pH 4, exact by addition of sulfuric acid, which converted pravastatin back to its free acid. The i-butyl acetate phase, containing pravastatin, was washed with water (5×10 ml). Pravastatin was then converted to its sodium salt and back-extracted into another aqueous phase by swirling the i-butyl acetate solution over water between about 900–2700 ml with intermittent addition of 8 m NaOH until a pH of between about pH 7.4 to about pH 13 was reached.

The pravastatin sodium salt solution was then treated with an ion exchange resin to scavenge excess sodium cations. After separation, the aqueous phase was stirred over IRC 50 in the $H^+$ ion exchange resin for 30 min. at ambient temperature. Stirring was continued until a pH of about pH 7.4 to about pH 7.8 was reached.

The solution was then filtered to remove the resin and partially concentrated to a weight of 508 g. under vacuum. Acetonitrile (480 ml) was then added and the solution was stirred over activated carbon (5 g) to decolorize. Pravastatin sodium was obtained as crystals by crystallization in 90% yield after further addition of acetone and acetonitrile to form a 1/3/12 mixture of water/acetone/acetonitrile (5.9 L) with cooling to about −10 to about 0° C. Pravastatin sodium was obtained in an overall yield of 65% in about 99.8% purity from the starting fermented active substance as measured by HPLC using the above-described conditions.

Example 2

Following the procedure in Example 1, but omitting the recrystallization from the water/acetone/acetonitrile mixture, pravastatin sodium was obtained by lyophilization of the concentrated solution of pravastatin sodium in water in about 99% purity and about 72% yield.

Example 3

Following the procedure of Example 1, but further purifying the pravastatin ammonium salt by once repeating the crystallization of the pravastatin ammonium salt, pravastatin sodium was obtained in about 99.8% purity and 68.4% yield.

Example 4

Following the procedure of Example 1, but further purifying the pravastatin ammonium salt by twice repeating the crystallization of the pravastatin ammonium salt, pravastatin sodium was obtained in about 99.6% purity and 53% yield.

Example 5

Following the procedure of Example 1, the fermentation broth (100 L) was acidified to pH from about 2.5 to about 5.0. by addition of sulfuric acid. The acidified fermentation broth was extracted with i-butyl acetate (3×50 L). The combined i-butyl acetate phases were then extracted with water (35 L) having been basified to a pH of about pH 7.5 to about pH 11.0 by addition of concentrated ammonium hydroxide.

Instead of reacidifying the aqueous extract and extracting with i-butyl acetate to obtain a further enriched organic solution as was done in Example 1, the aqueous extract was concentrated to 140 g/L under vacuum. The resulting concentrated solution was then acidified to a pH of about pH 4.0 to about pH 7.5 by addition of 1M HCl.

Ammonium chloride crystals (405 g.) were then added to the concentrated solution and the pravastatin ammonium salt was allowed to crystallize at ambient temperature. The crystals were then isolated by filtration and washed with a saturated solution of ammonium chloride. The crystals were then added to water (1L) at 40° C. After dissolution, the temperature was reduced to 30° C. and ammonium chloride (330 g.) was added to the solution. The solution was then stirred for 15 h at ambient temperature and crystals of pravastatin ammonium salt were recovered by filtration and washed with i-butyl acetate and after that with acetone and dried. The resulting crystals were then further purified by recrystallization transposed to the sodium salt and isolated as described in Example 1. Pravastatin sodium was obtained in about 99.9% purity and 67.7% yield.

Example 6

Following the procedure of Example 1, but the pravastatin sodium salt was crystallized from 1/15 mixture of water/acetone in an overall yield from the starting fermented active substance of 64% and in 99.8% purity as measured by HPLC.

Example 7

Following the method of Example 5, first two paragraphs, a concentrated aqueous extract (140 g. $L^{-1}$) was obtained. The concentrated aqueous extract was divided into equal parts.

Example 8

Following the procedure in Example 1, pravastatin ammonium salt was isolated from a fermentation broth, but active substance was dissolved and crystallized after precipitation with ammonia gas.

Enriched pravastatin i-butyl acetate solution (6500 L) was decolorized over activated charcoal (6.5 kg). Then the solution was filtered to remove the charcoal and transferred to a vessel equipped with a gas inlet.

The solution contained 183.2 kg active substance.

Pravastatin ammonium salt was precipitated with ammonia gas following the procedure in Example 1.

Precipitated pravastatin ammonium salt was dissolved by adding water (1099 L) to the vessel in presence of i-butyl acetate mother liquor.

Pravastatin ammonium salt was crystallized by adding ammonium chloride (412 kg) into the vessel. Ammonium chloride was added in 31 parts at 30–32° C. during 5 hours. The suspension was stirred at 24–26° C. for 1 hour. Crystals were filtered, suspended in i-butyl acetate and filtered then suspended in i-butyl acetate: acetone (2:1) and filtered, then suspended in acetone and filtered. Crystals were dried in vacuum after washing with acetone.

The process yielded pravastatin ammonium salt in about 93% purity as determined by HPLC with UV detection at 1=238 nm. Crystallized active substance was 168.7 kg.

Example 9

Following the procedure in Example 1, pravastatin ammonium salt was isolated from a fermentation broth, but crystallization was used instead of precipitation with ammonia gas.

Enriched pravastatin i-butyl acetate solution (4150 ml) was decolorized over activated charcoal (4.15 g). Then the solution was filtered to remove the charcoal and transferred into a flask.

Water (300 ml) was added to i-butyl acetate solution. pH was adjusted to 9.36 with conc. ammonia solution (27 ml).

Pravastatin ammonium salt was crystallized by adding ammonium chloride (121.5 g) into the flask. Ammonium chloride was added in more parts at 30–32° C. during 5 hours. The suspension was stirred at 24–26° C. for 15 hours. Crystals were filtered, more times suspended, washed and dried.

The process yielded pravastatin ammonium salt in about 95% purity as determined by HPLC. Crystallized active substance was 42.7 g.

Example 10

Following the procedure of Example 8, pravastatin ammonium salt was produced in about 93% purity.

Active substance (10 g) was dissolved in water (60 ml): acetone (6 ml): isobutyl acetate (6 ml) mixture at 35–40° C. The solution was cooled to 30–32° C. Ammonium chloride (22 g) was added into the solution in more parts during 5 hours.

The suspension was cooled to 24–26° C. and it was stirred for an hour then pravastatin ammonium salt was filtered, washed with isobutyl acetate then with acetone. Pravastatin ammonium salt was dried at 40° C. The yield was 96%. The purity was 97%.

Example 11

Following the procedure of Example 8, pravastatin ammonium salt was produced in about 93% purity.

Active substance (10 g) was dissolved in water (60 ml): acetone (6 ml): isobutyl acetate (6 ml) mixture at 35–40° C. The solution was cooled to 30–32° C. Sodium chloride (11.4 g) was added into the solution in more parts during 3 hours.

Pravastatin sodium salt was filtered, washed with isobutyl acetate then with acetone then it was dried at 40° C.

The yield was 77%. The purity was 97%.

Example 12

Following the procedure of Example 8, pravastatin ammonium salt was produced in about 93% purity.

Active substance (10 g) was dissolved in water (60 ml): acetone (6 ml): isobutyl acetate (6 ml) mixture at 35–40° C. The solution was cooled to 30–32° C. Lithium chloride (9.3 g) was used for salting out crystallization.

Filtered pravastatin lithium salt was washed with isobutyl acetate and dried. Pravastatin lithium salt was obtained in 96% purity with 89% yield.

We claim:

1. Pravastatin sodium having a purity of 99% to 99.9%.

2. Pravastatin sodium containing less than 0.2% epipravastatin.

3. The pravastatin sodium of claim 2, further containing less than 0.5% pravastatin lactone.

4. The pravastatin sodium of claim 2, further containing less than 0.1% epipravastatin sodium.

5. The pravastatin sodium of claim 4, further containing less than 0.2% pravastatin lactone.

6. The pravastatin sodium of claim 1 containing less than 0.2% epipravastatin.

7. The pravastatin sodium of claim 6, further containing less than 0.5% pravastatin lactone.

8. The pravastatin sodium of claim 6 containing less than 0.1% epipravastatin.

9. The pravastatin sodium of claim 8, further containing less than 0.2% pravastatin lactone.

* * * * *

UNITED STATES PATENT AND TRADEMARK OFFICE
CERTIFICATE OF CORRECTION

PATENT NO. : 6,936,731 B2
APPLICATION NO. : 09/971746
DATED : August 30, 2005
INVENTOR(S) : Vilmos Keri et al.

It is certified that error appears in the above-identified patent and that said Letters Patent is hereby corrected as shown below:

In the Abstract, line 6, replace "an solution" with --a solution--;

Column 2, line 15, replace "fermenation" with --fermentation--;

line 63, replace "*Steptomyces*" with --*Streptomyces*--;

Column 3, line 12, replace "pravaststin" with --pravastatin--;

Column 5, line 54, replace "advantages" with --advantageous--;

line 65, replace "transfered" with --transferred--;

Column 6, line 18, replace "DLAION" with --DIAION--;

Column 7, line 16, replace "1 and 3" with --1 and 3.--;

Column 8, line 14, replace "enteric-coating" with --enteric coating--.

Column 12, line 25, claim 1, cancel the text "1. Pravastatin sodium having a purity of 99% to 99.9%".;

line 26, claim 2, replace "2." with --1.--;

line 28, claim 3, replace "3. The pravastatin sodium of claim 2" with --2. The pravastatin sodium of claim 1--;

lines 30-31, claim 4, replace "4. The pravastatin sodium of claim 2, further containing less than 0.1% epipravastatin sodium." with --3. The pravastatin sodium of claim 1 containing less than 0.1% epipravastatin.--;

line 32, claim 5, replace "5. The pravastatin sodium of claim 4" with --4. The pravastatin sodium of claim 3--;

lines 34-35, claim 6, replace "6. The pravastatin sodium of claim 1 containing less than 0.2% epipravastatin." with --5. The pravastatin sodium of claim 1 having a purity of 99% to 99.9%.--;

line 36, claim 7, replace "7. The pravastatin sodium of claim 6" with --6. The pravastatin sodium of claim 5--;

UNITED STATES PATENT AND TRADEMARK OFFICE
CERTIFICATE OF CORRECTION

PATENT NO. : 6,936,731 B2
APPLICATION NO. : 09/971746
DATED : August 30, 2005
INVENTOR(S) : Vilmos Keri et al.

It is certified that error appears in the above-identified patent and that said Letters Patent is hereby corrected as shown below:

Column 12, (cont'd)

line 38, claim 8, replace "8. The pravastatin sodium of claim 6" with -- 7. The pravastatin sodium of claim 5--; and line 40, claim 9, replace "9. The pravastatin sodium of claim 8" with --8. The pravastatin sodium of claim 7--.

Signed and Sealed this

Tenth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,936,731 B2
APPLICATION NO. : 09/971746
DATED : August 30, 2005
INVENTOR(S) : Vilmos Keri et al.

It is certified that error appears in the above-identified patent and that said Letters Patent is hereby corrected as shown below:

Title Page
In the Abstract, line 6, replace "an solution" with --a solution--;

Column 2, line 15, replace "fermenation" with --fermentation--;

line 63, replace "*Steptomyces*" with --*Streptomyces*--;

Column 3, line 12, replace "pravaststin" with --pravastatin--;

Column 5, line 54, replace "advantages" with --advantageous--;

Line 65, replace "transfered" with --transferred--;

Column 6, line 18, replace "DLAION" with --DIAION--;

Column 7, line 16, replace "1 and 3" with --1 and 3.--;

Column 8, line 14, replace "enteric-coating" with --enteric coating--.

Column 12, line 25, claim 1, cancel the text "1. Pravastatin sodium having a purity of 99% to 99.9%.";

line 26, claim 2, replace "2." with --1.--;

line 28, claim 3, replace "3. The pravastatin sodium of claim 2" with --2. The pravastatin sodium of claim 1--;

lines 30-31, claim 4, replace "4. The pravastatin sodium of claim 2, further containing less than 0.1% epipracastatin sodium." with --3. The pravastatin sodium of claim 1 containing less than 0.1% epipracastatin.--;

line 32, claim 5, replace "5. The pravastatin sodium of claim 4" with --4. The pravastatin sodium of claim 3--;

lines 34-35, claim 6, replace "6. The pravastatin sodium of claim 1 containing less than 0.2% epipravastatin." with --5. The pravastatin sodium of claim 1 having a purity of 99% to 99.9%.--;

line 36, claim 7, replace "7. The pravastatin sodium of claim 6" with --6. The pravastatin sodium of claim 5--;

UNITED STATES PATENT AND TRADEMARK OFFICE
CERTIFICATE OF CORRECTION

PATENT NO. : 6,936,731 B2
APPLICATION NO. : 09/971746
DATED : August 30, 2005
INVENTOR(S) : Vilmos Keri et al.

It is certified that error appears in the above-identified patent and that said Letters Patent is hereby corrected as shown below:

Column 12, line 38, claim 8, replace "8. The pravastatin sodium of claim 6" with --7. The pravastatin sodium of claim 5--; and line 40, claim 9, replace "9. The pravastatin sodium of claim 8" with --8. The pravastatin sodium of claim 7--.

Signed and Sealed this

Fourteenth Day of November, 2006

JON W. DUDAS
*Director of the United States Patent and Trademark Office*